US012594130B2

(12) United States Patent
Demanget et al.

(10) Patent No.: US 12,594,130 B2
(45) Date of Patent: Apr. 7, 2026

(54) ROBOT ARRAY

(71) Applicant: DEPUY IRELAND UNLIMITED COMPANY, County Cork (IE)

(72) Inventors: Nicolas Demanget, Cambridge, MA (US); Alasdair Mercer, Leeds (GB)

(73) Assignee: DEPUY IRELAND UNLIMITED COMPANY, County Cork (IE)

( * ) Notice: Subject to any disclaimer, the term of this patent is extended or adjusted under 35 U.S.C. 154(b) by 313 days.

(21) Appl. No.: 18/361,265

(22) Filed: Jul. 28, 2023

(65) Prior Publication Data

US 2024/0065775 A1 Feb. 29, 2024

Related U.S. Application Data

(60) Provisional application No. 63/373,615, filed on Aug. 26, 2022.

(51) Int. Cl.
| | |
|---|---|
| *A61B 34/20* | (2016.01) |
| *A61B 34/30* | (2016.01) |
| *B25J 9/16* | (2006.01) |
| *A61B 46/10* | (2016.01) |

(52) U.S. Cl.
CPC .............. *A61B 34/20* (2016.02); *A61B 34/30* (2016.02); *B25J 9/1697* (2013.01); *A61B 2034/2055* (2016.02); *A61B 46/10* (2016.02)

(58) Field of Classification Search
CPC .. A61B 2017/00477; A61B 2034/2055; A61B 2090/3983; A61B 34/20; A61B 34/30; A61B 46/10; A61B 90/39; B25J 9/1697
See application file for complete search history.

(56) References Cited

U.S. PATENT DOCUMENTS

| | | | |
|---|---|---|---|
| 7,643,862 | B2 | 1/2010 | Schoenefeld |
| 9,452,023 | B2 | 9/2016 | Boillot |
| 11,109,777 | B2 | 9/2021 | Stein |
| 11,123,253 | B2 | 9/2021 | Anderson |
| 11,141,227 | B2 | 10/2021 | Shoham |
| 11,191,594 | B2 | 12/2021 | Morgan |
| 11,224,443 | B2 | 1/2022 | Amiot |

(Continued)

FOREIGN PATENT DOCUMENTS

| | | |
|---|---|---|
| AU | 2020201097 A1 | 9/2020 |
| EP | 2598074 A1 | 6/2013 |

(Continued)

OTHER PUBLICATIONS

Brainlab: "CIRQ—Robotics," https://www.advancedneurosurgery.com.au/pdfs/cirf-brainlab-robotics.pdf, XP093098113, Sep. 1, 2019.

(Continued)

*Primary Examiner* — Scott Luan
(74) *Attorney, Agent, or Firm* — Kramer & Amado, P.C.

(57) ABSTRACT

A surgical system, including: surgical robot; a connection member connected to the surgical robot; a drape; a plurality of tracking array assemblies configured to engage the connection member wherein the plurality of tracking array assemblies provide different fields of view for a tracking system and wherein the drape is configured to be placed between the connection member and the plurality of tracking array assemblies.

21 Claims, 10 Drawing Sheets

(56) References Cited

U.S. PATENT DOCUMENTS

| | | | | |
|---|---|---|---|---|
| 11,229,520 | B2 | 1/2022 | Fanson | |
| 11,298,196 | B2 | 4/2022 | Crawford | |
| 2007/0016009 | A1 | 1/2007 | Lakin | |
| 2008/0200794 | A1 | 8/2008 | Tiechman | |
| 2015/0297314 | A1 | 10/2015 | Fowler | |
| 2019/0099232 | A1 | 4/2019 | Soto | |
| 2020/0069372 | A1 | 3/2020 | Dufour | |
| 2021/0007809 | A1 | 1/2021 | Morgan | |
| 2021/0113294 | A1 | 4/2021 | Collet | |
| 2021/0128250 | A1 | 5/2021 | Chav | |
| 2021/0186711 | A1 | 6/2021 | van der Walt | |
| 2021/0330273 | A1* | 10/2021 | Crawford | A61B 6/487 |
| 2021/0369349 | A1 | 12/2021 | Haider | |
| 2022/0008137 | A1* | 1/2022 | Brik | A61B 34/30 |
| 2022/0040855 | A1 | 2/2022 | Cha | |
| 2022/0096166 | A1 | 3/2022 | Couture | |
| 2022/0125517 | A1 | 4/2022 | Zimmermann | |
| 2022/0125520 | A1 | 4/2022 | Crawford | |

FOREIGN PATENT DOCUMENTS

| | | | |
|---|---|---|---|
| EP | 3033024 | A1 | 6/2016 |
| EP | 3409231 | A1 | 12/2018 |
| EP | 3419544 | A1 | 1/2019 |
| EP | 3878393 | A2 | 9/2021 |
| EP | 2720631 | B1 | 1/2022 |
| EP | 3936075 | A2 | 1/2022 |
| EP | 3937825 | A1 | 1/2022 |
| EP | 3977949 | A1 | 4/2022 |
| WO | 2020185930 | A1 | 9/2020 |

OTHER PUBLICATIONS

Mirza Pojskic et al., "Initial Intraoperative Experience with Robotic-Assisted Pedicle Screw Placement with Cirq Robotic Alignment: An Evaluation of the First 70 Screws", Journal of Clinical Medicine, vol. 10, No. 24, Dec. 7, 2021, p. 5725.
International Search Report & Written Opinion for PCT/EP2023/073239 mailed on Feb. 15, 2024.

* cited by examiner

ROBOT ARRAY

CROSS-REFERENCE TO RELATED APPLICATION

This application claims the benefit of U.S. Provisional Patent Application No. 63/373,615, filed Aug. 26, 2022, which is incorporated, for all purposes, by reference herein in its entirety.

TECHNICAL FIELD

Various exemplary embodiments disclosed herein relate to robot arrays used for tracking during robot surgery.

BACKGROUND

Computer assisted surgical systems have been developed in order for a surgeon to carry out various steps in surgery accurately and in a reduced time. For example, in various orthopedic surgeries, various cuts need to be accurately made. Such accuracy is very important, for example, with various joint surgeries (e.g., knee, shoulder, hip, ankle, wrist, etc.) when the joints are to be replaced or repaired. Robotic systems have been developed to assist in such surgeries. These robotic systems may include tools that are mounted to the robot and then guided to a precise location to perform a function on the patient such as cutting, drilling, milling, etc. Such operations using tools will carry out planned operation on the patient. In order to carry out these operations the location of the tool and specifically the cutting/drilling/milling portion of the tool needs to be very accurately known relative to the patient.

The system may include a tracking unit that is configured to determine in real time the location and orientation of the tool relative to the patient. The tracking unit may detect the location of tracking arrays attached to the patient and the tool. The location of a tracking array on the patient is known relative to the anatomy of the patient. Then the tracking unit may detect and track the tracking arrays on the patient and the tool, which allows the system to know the precise location of the tool including a cutting surface relative to the patient.

In planning the surgery, a path of the cutting surface of the tool is planned. Then actuators in the robot move the tool along the desired path using the tracking system to ensure that the path is correctly and accurately followed. Then the cutting/drilling/milling or other operation may be carried out on the patient anatomy at the desired location on the patient anatomy.

SUMMARY

A summary of various exemplary embodiments is presented below. Some simplifications and omissions may be made in the following summary, which is intended to highlight and introduce some aspects of the various exemplary embodiments, but not to limit the scope of the invention. Detailed descriptions of an exemplary embodiment adequate to allow those of ordinary skill in the art to make and use the inventive concepts will follow in later sections.

Various embodiments relate to a surgical system, including: surgical robot; a connector coupled to the surgical robot, the connector configured and adapted to mate with tracking array assemblies; a line-of-sight spatial camera; a first tracking array assembly having a plurality of first trackers, the first tracking array assembly configured to mate with the connector wherein when the first tracking array assembly is mated to the connector the plurality of first trackers are located in first spatial positions relative to the surgical robot, the plurality of first trackers configured to be visible to the line-of-sight spatial camera; and a second tracking array assembly having a plurality of second trackers, the second tracking array assembly configured to mate with the connector wherein when the second tracking array assembly is mated to the connector the plurality of second trackers are located in second spatial positions relative to the surgical robot, the plurality of second trackers configured to be visible to the line-of-sight spatial camera wherein the first spatial positions relative to the surgical robot are different from the second spatial positions relative to the surgical robot, wherein the first tracking array assembly is configured and adapted for use in a first clinical application and the second tracking array assembly is configured and adapted for use in a second clinical application, wherein the first clinical application is different than the second clinical application.

Various embodiments are described, wherein a first tracking array assembly of the plurality of tracking array assemblies is configured to be used for a knee surgery.

Various embodiments are described, wherein a second tracking array assembly of the plurality of tracking array assemblies is configured to be used for a shoulder surgery.

Various embodiments are described, including a drape between the connector and one of the first tracking array assembly and the second tracking array assembly.

Further various embodiments relate to a tracking array assembly for use with a surgical system, including: a body with a window configured to view a connection member when the tracking array assembly is connected to the connection member; a locking mechanism on the body including locking handles configured to engage the connection member and to securely fasten the tracking array assembly to the connection member; a first tracking element on the body; a frame extending from the body; and a second tracking element and a third tracking element on the frame.

Various embodiments are described, wherein the body includes an attachment opening formed by the locking handles and body extensions.

Various embodiments are described, wherein locking handles include a locking edge configured to grip an engagement surface of the connection member.

Various embodiments are described, wherein locking handles are rotatably connected to the body and configured to actuated to disconnect the tracking array assembly from the connection member.

Further various embodiments relate to a tracking array assembly for use with a surgical system, including: a body with a window configured to view a connection member when the tracking array assembly is connected to the connection member; a locking mechanism on the body including locking handles configured to engage the connection member and to securely fasten the tracking array assembly to the connection member; three tracking elements on the body; and an attachment opening on the body.

Various embodiments are described, wherein locking handles include a locking edge configured to grip an engagement surface of the connection member.

Various embodiments are described, wherein locking handles are rotatably connected to the body and configured to actuated to disconnect the tracking array assembly from the connection member.

Various embodiments are described, wherein ends of the locking handles that engage the connection member are rotatably connected to the body and configured to actuated to disconnect the tracking array assembly from the connection member.

Various embodiments are described, wherein the attachment opening lies within a triangle formed by the three tracking elements.

Various embodiments are described, wherein the attachment opening is substantially centered on the body.

Various embodiments are described, wherein the attachment opening is substantially centered among the three tracking elements.

Further various embodiments relate to a method of using a surgical system including; surgical robot; a connection member connected to the surgical robot; a drape; a first and second tracking array assemblies configured to engage the connection member wherein the first and second tracking array assemblies provide different fields of view for a tracking system and wherein the drape is configured to be placed between the connection member and the plurality of tracking array assemblies, including: determining that a surgery to be performed by the surgical system requires the use of the second tracking array assembly; removing the first tracking array assembly from the surgical robot; placing the drape over the connection member; attaching the second tracking array assembly to the surgical robot; and calibrating the surgical system using the second tracking array assembly.

Various embodiments are described, including performing the surgery using the second tracking array assembly Various embodiments are described, wherein the first tracking array assembly is used for knee surgery and the second tracking array assembly is used for a different surgery.

Various embodiments are described, wherein the different surgery is shoulder surgery.

Various embodiments are described, wherein the first tracking array assembly is used for shoulder surgery and the second tracking array assembly is used for a different surgery.

Various embodiments are described, wherein the different surgery is knee surgery.

Further various embodiments relate to a tracking array assembly for use with a surgical system, including: a tracking array including three tracking elements and an array connector; and a body including: a first arm configured to connect to the array connector of the tracking array; a second are configured to connect to the array connector of the tracking array; and a locking mechanism configured to engage a robot connector and to securely fasten the body to the robot connector.

Various embodiments are described, wherein the tracking array is connected to one of the first arm and the second arm depending upon the location of surgery on a patient.

Further various embodiments relate to a computer assisted surgical system, including: a surgical robot; a line-of-sight spatial camera; and a computer system configured to: detect a type of tracking array attached to the surgical robot; determine a surgical procedure associated with the detected type of tracking array; and automatically perform functions associated with the determined surgical procedure.

BRIEF DESCRIPTION OF THE DRAWINGS

In order to better understand various exemplary embodiments, reference is made to the accompanying drawings in the following listing.

To facilitate understanding, identical reference numerals have been used to designate elements having substantially the same or similar structure and/or substantially the same or similar function.

DETAILED DESCRIPTION

The description and drawings illustrate the principles of the invention. It will thus be appreciated that those skilled in the art will be able to devise various arrangements that, although not explicitly described or shown herein, embody the principles of the invention and are included within its scope. Furthermore, all examples recited herein are principally intended expressly to be for pedagogical purposes to aid the reader in understanding the principles of the invention and the concepts contributed by the inventor(s) to furthering the art and are to be construed as being without limitation to such specifically recited examples and conditions. Additionally, the term, "or," as used herein, refers to a non-exclusive or (i.e., and/or), unless otherwise indicated (e.g., "or else" or "or in the alternative"). Also, the various embodiments described herein are not necessarily mutually exclusive, as some embodiments can be combined with one or more other embodiments to form new embodiments.

Figure 1A:
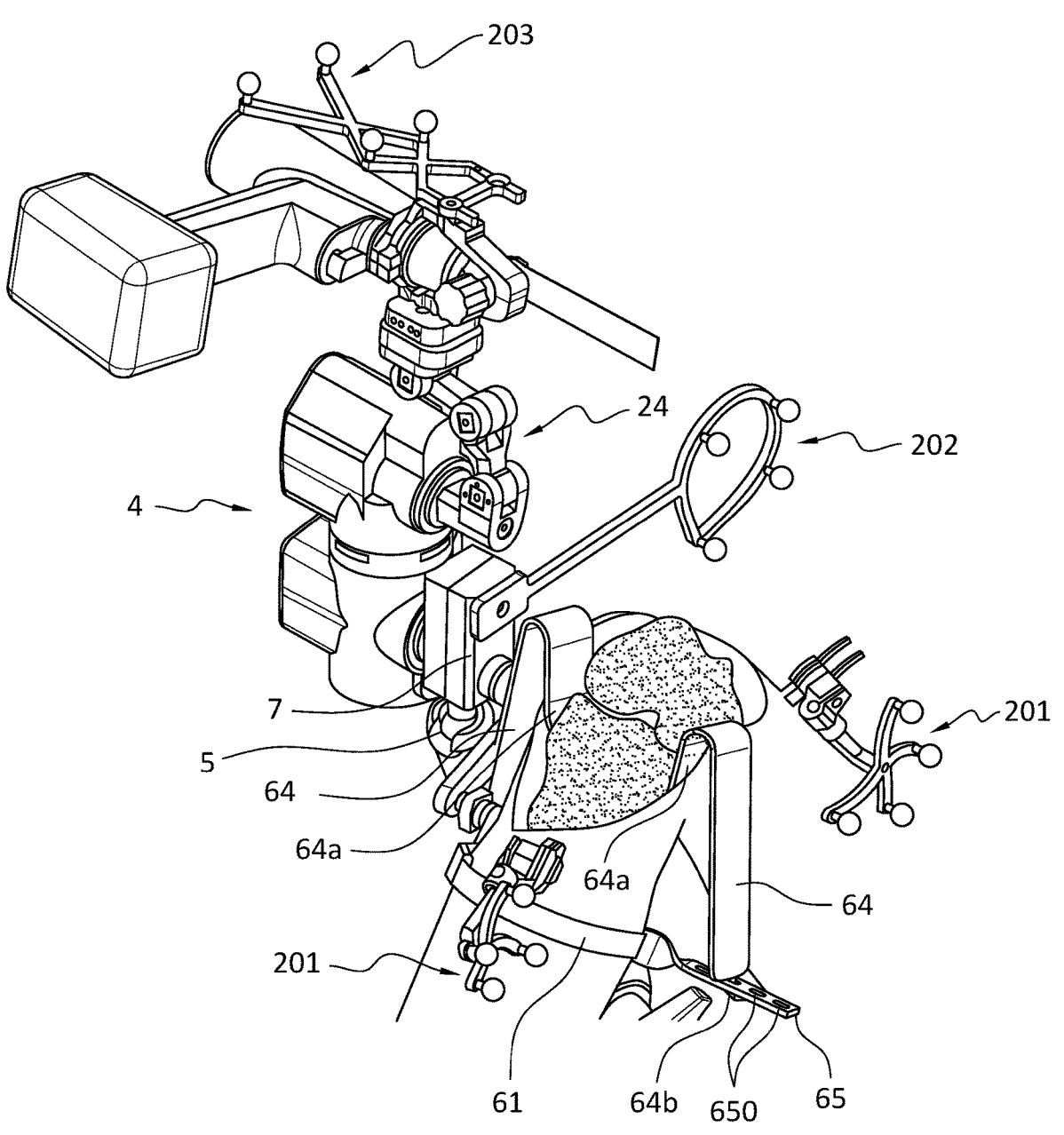
FIG. 1A illustrates a knee surgery being performed using a robot.

FIG. 1A illustrates a knee surgery being performed using a robot. FIG. 1A is FIG. 13 in U.S. Patent Publication No. 20210353311 (the '311 publication) which is hereby incorporated herein by reference for all purposes. FIG. 1A illustrates an actuator unit 4 that has a saw 2 attached to perform a cut on the knee. Trackers 201 are attached to the femur and the tibia. These trackers track the location of the femur and the tibia. A tracker 203 is attached to the cutting tool to track the location of the cutting tool. Also, a tracker 202 is attached to the second segment of the actuation unit 4. This allows for the location of the actuation unit to be tracked. A tracking unit is used to track the location of each of trackers 201, 202, and 203. It is noted that the tracker 202 includes a long arm that extends away from the actuation unit 4 so that the tracking unit may have an unobstructed view of the tracker 202, because if the tracker 202 were closer to the second segment of the actuation unit 4, the tracking units view of the tracker 202 may be obstructed by the knee.

Figure 1B:
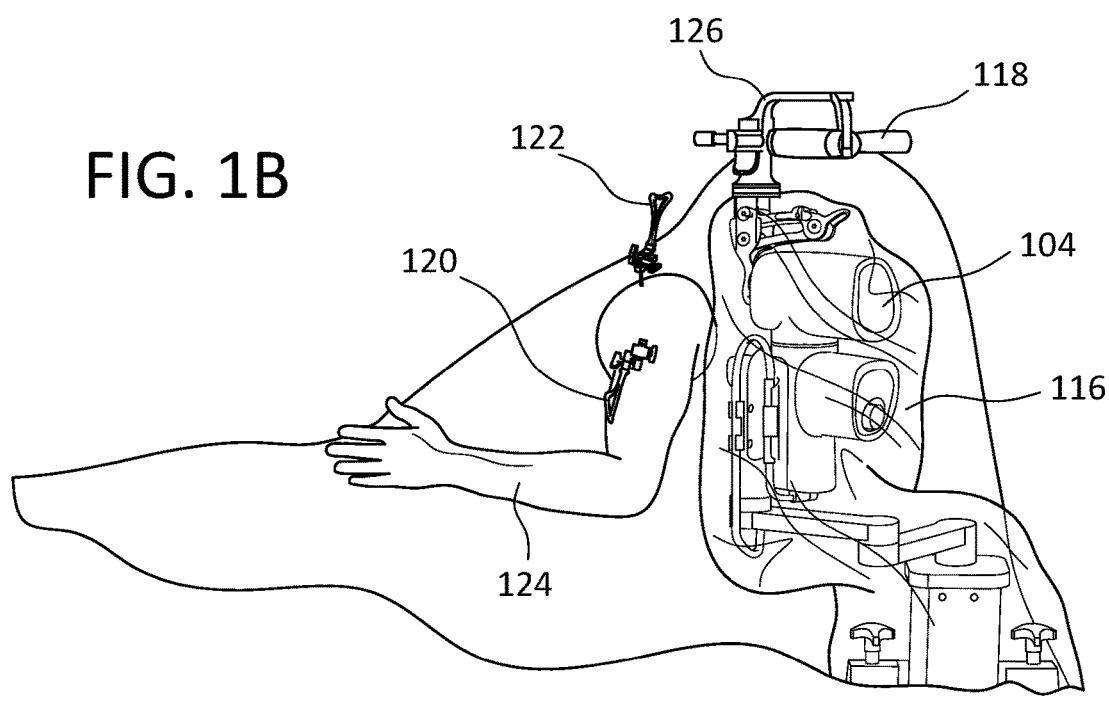
FIGS. 1B and 1C illustrate the robot system with a surgical tool in two different positions near the patient.
Figure 1C:
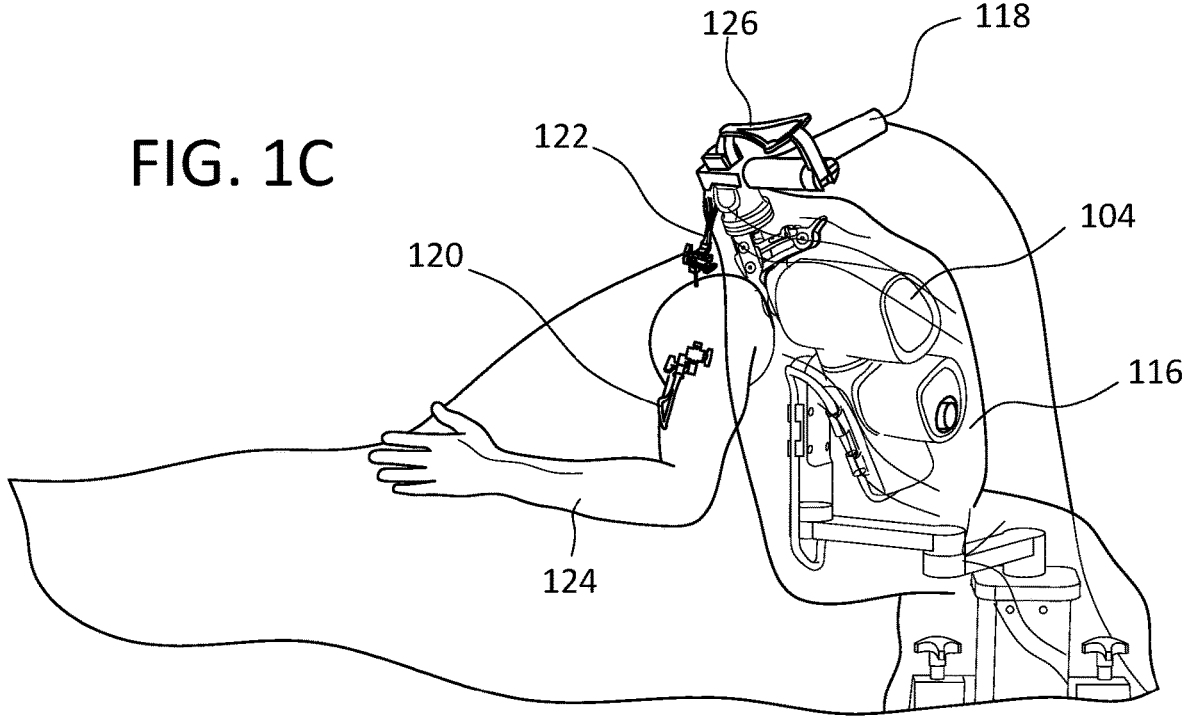

FIGS. 1B and 1C illustrate the robot system 104 with a surgical tool 118 in two different positions near the patient 124. The robot system 104 includes a connection member 300 that receives and connects to the tracking array 500. The knee tracking array assembly 202 is on an arm in order to be seen by the tracking system. In the case of a shoulder surgery the use of the knee tracking array assembly 202 would make it difficult for the tracking system to see the knee tracking array assembly 202. Accordingly, tracking arrays as illustrated in FIGS. 4A-4D, 5A-5D, and 6A-6B may be used instead for shoulder or other surgeries with a similar field of view. These tracking arrays will be further described below.

Figures 2A, 2B:
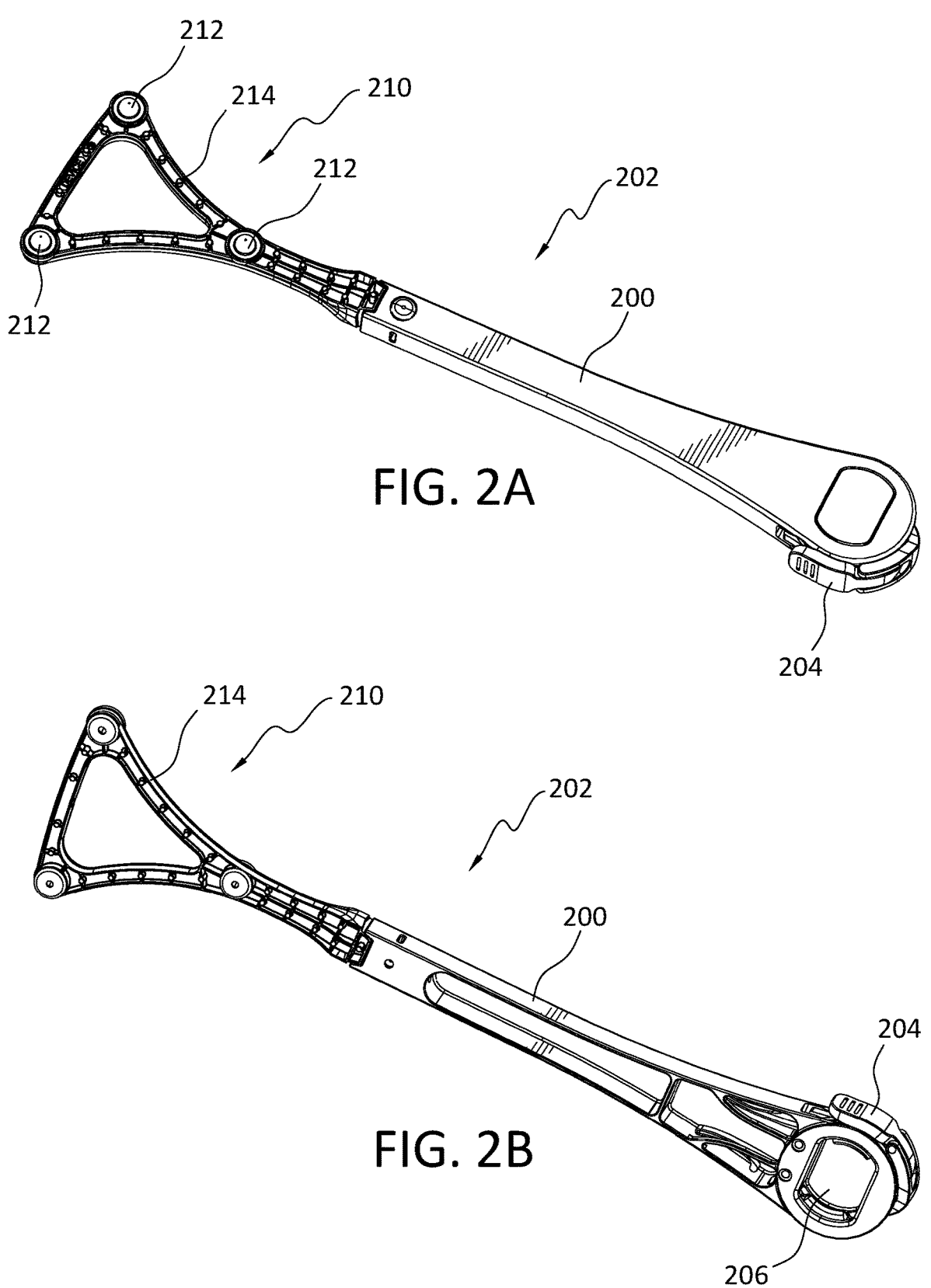
FIGS. 2A and 2B illustrate a top perspective and bottom perspective view an embodiment of knee tracking array assembly used during knee surgery.

FIGS. 2A and 2B illustrate a top perspective and bottom perspective view an embodiment of knee tracking array assembly used during knee surgery. While the knee tracking array 204 is described for use in a knee surgery, it may also be applied to other surgeries with a similar field of view. The knee tracking array assembly 202 includes a tracking arm 200 and a tracking array 210. The tracking arm 200 allows for the tracking array 210 to be located away from the robot so that it is in the field of view of the camera in the tracking system during a knee surgery. Accordingly, the length of the tracking arm 200 is selected to be within the field of view of the camera and not obstructed by the patient, the surgical tool, or the surgeon. The tracking arm 200 may include an attachment opening 206 that engages a connection member 300 (see FIGS. 3A-3D) extending from the surgical robot. A locking lever 204 actuates a locking mechanism that engages the connection member 300 to securely fasten the knee tracking array assembly 202 to the connection member 300. The attachment opening 206 has a shape that is complementary to the shape of the connection member 300 so as to properly orient the knee tracking array assembly 202 and to ensure a secure connection. Also, a drape may be placed over connection head 300 before the knee tracking array assembly 202 is attached to the connection head 300. This provides sterile barrier between the patient 124 and the surgical robot.

Figure 2C:
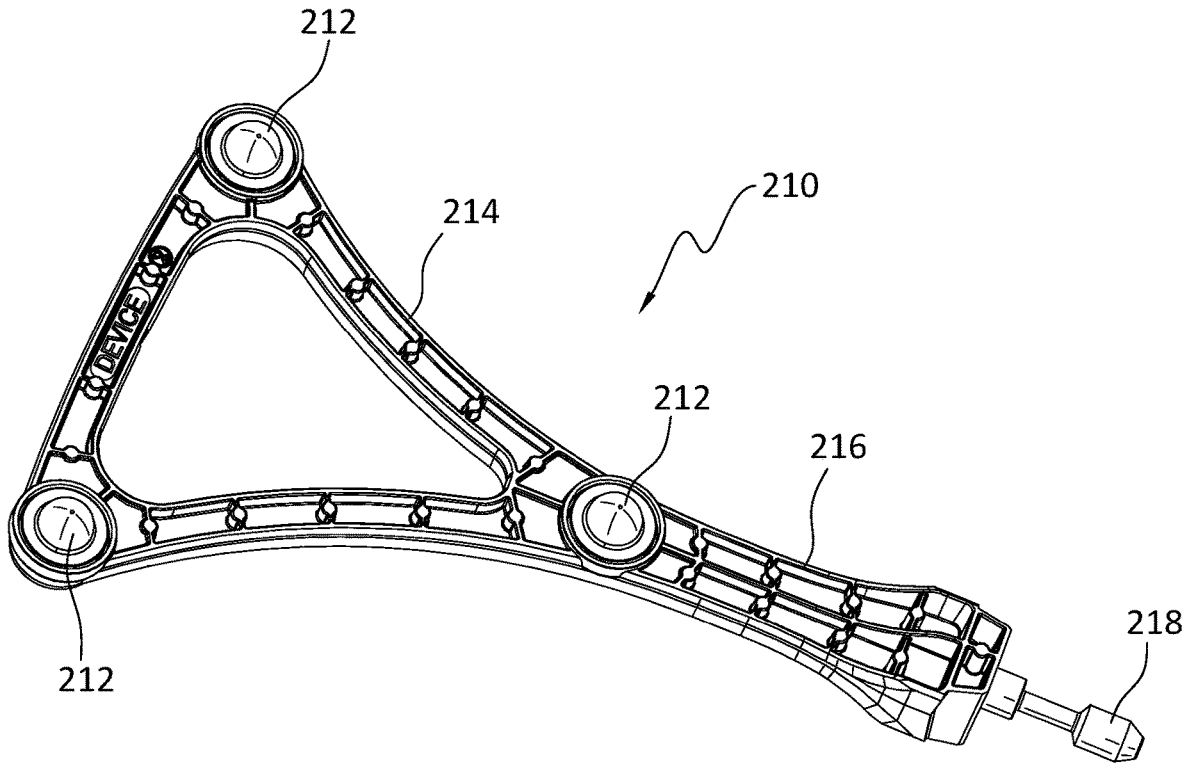
FIG. 2C illustrates a perspective view of the tracking array.
Figures 3A, 3B, 3C, 3D:
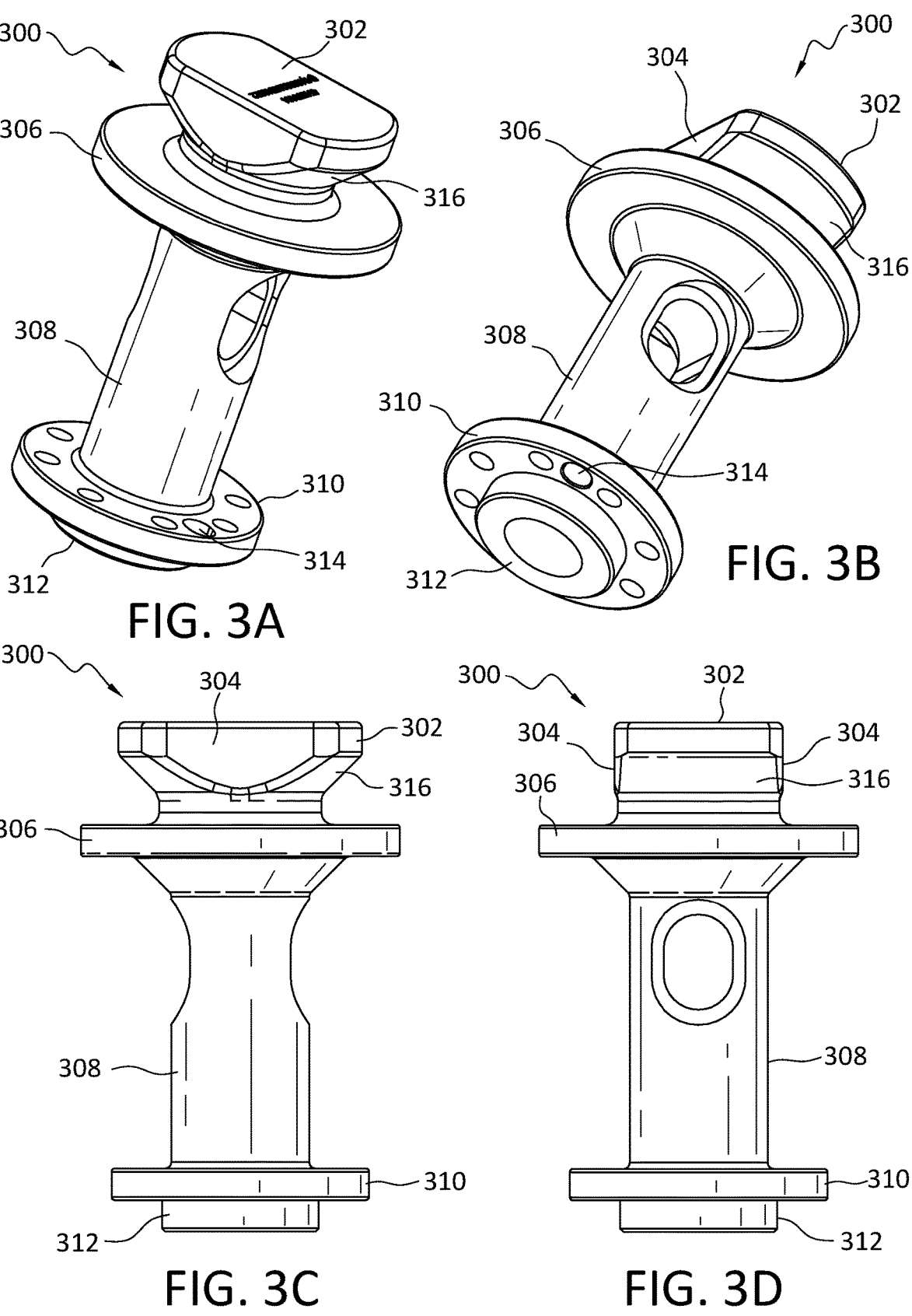
FIGS. 3A-D illustrate top perspective, bottom perspective, first side, and second side views of an embodiment of a connection member.
Figure 4A:
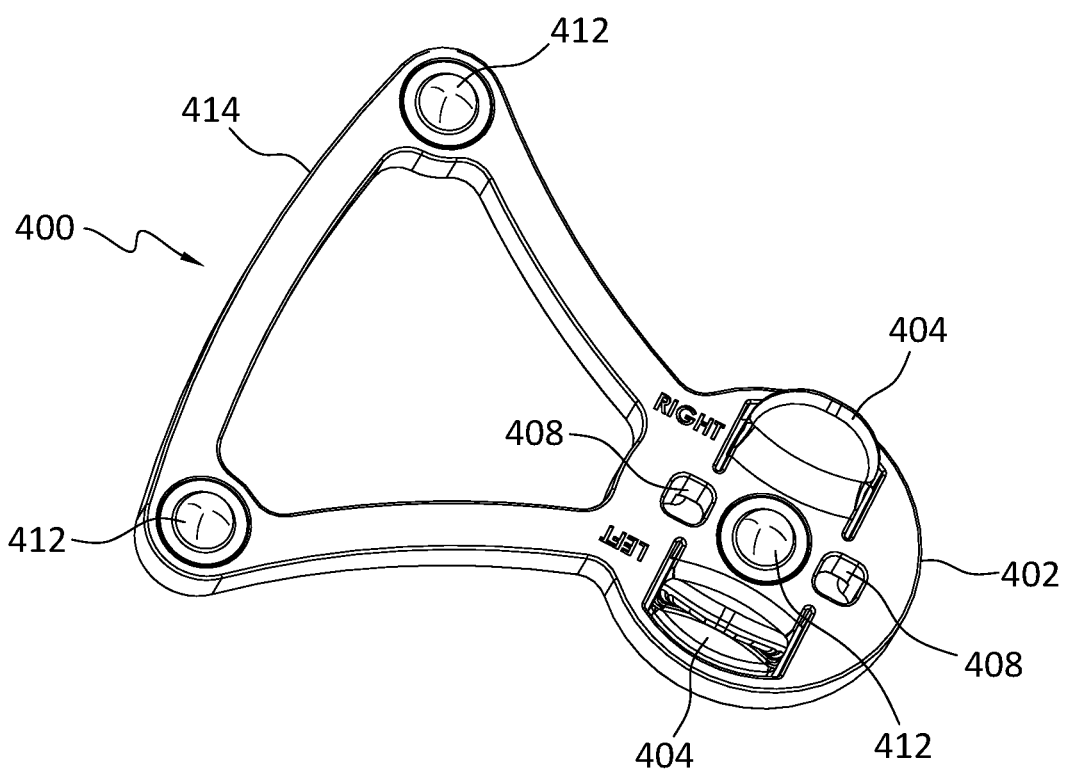
FIGS. 4A-D illustrate top perspective, bottom perspective, top, and bottom views, respectively, of a first embodiment of a tracking array that may be used in shoulder or other robotic surgeries.
Figure 4B:
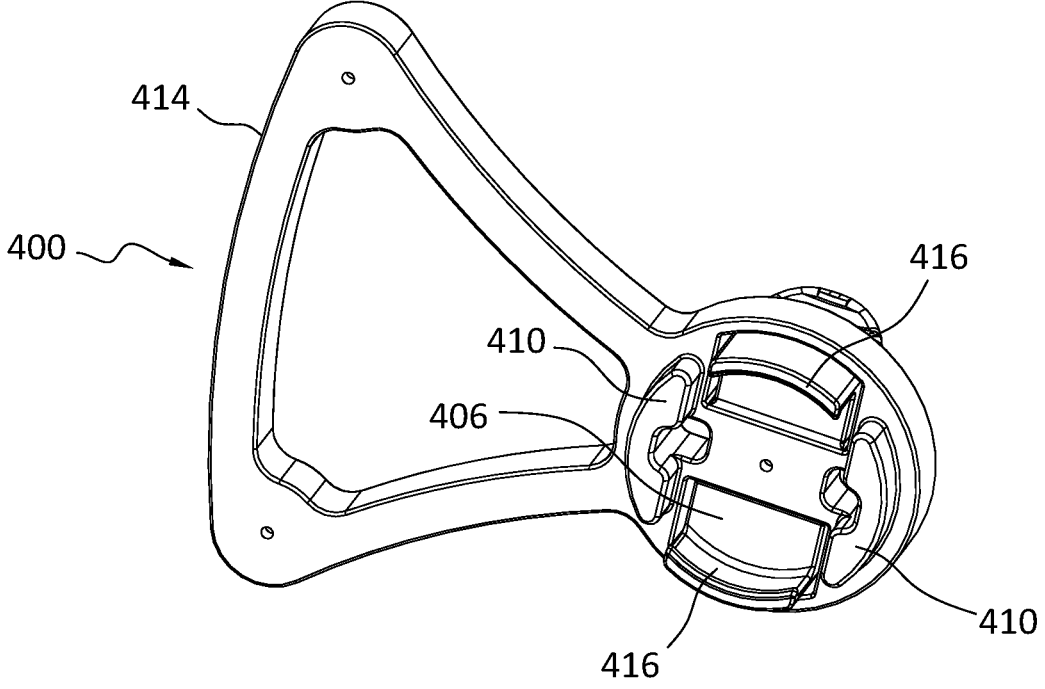
Figures 4C, 4D:
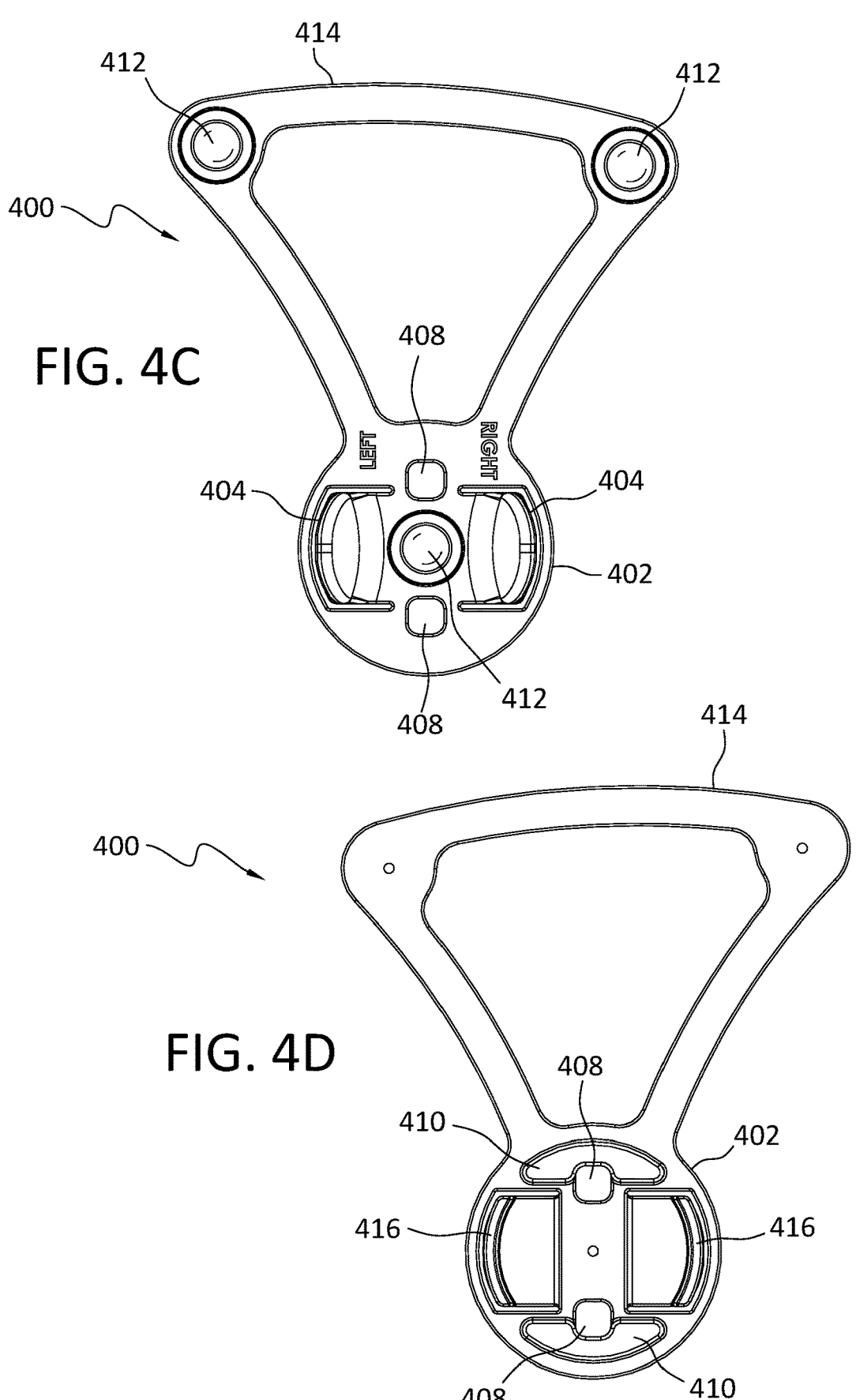

FIG. 2C illustrates a perspective view of the tracking array. The tracking array 210 includes tracking elements 212, array frame 214, array arm 216, and array connector 218. The tracking elements 212 may be active or passive tracking elements as described above. The tracking array 210 will typically have at least three tracking elements to provide complete location and orientation information of the tracking array 210. The tracking elements 212 are mounted on a generally triangular array frame 214. The array frame 214 may take other shapes as well depending upon the specific application and the number of tracking elements 212. The array arm 216 is optional and provides additional length for the knee tracking array assembly 202. The array connector 218 engages the tracking arm 200. This allows for different tracking arrays 210 to be used or for the tracking array 210 to be replaced or removed during the procedure if needed. In other embodiments, the tracking array 210 and the tracking arm 200 may be formed as a single integral structure.

FIGS. 3A-D illustrate top perspective, bottom perspective, first side, and second side views of an embodiment of a connection member. The connection member 300 connects the knee tracking array assembly 202 or other tracking assembly to the surgical robot. The connection member 300 includes a connection head 302, upper collar 306, body 308, and lower collar 310. The connection head 302 engages the attachment opening 206 in the attached tracking assembly. The connection head 302 may include flat surfaces 304 that help to align connection member 300 with the attached tracking assembly. Further, the general shape of the connection head 302 is complementary to the general shape of the attachment opening 206 in the attached tracking assembly. Further, the connection head 302 may have engagement surfaces 316 that may engage a locking mechanism in the attached tracking assembly to facilitate a secure connection between the connection member 300 and the attached tracking assembly. The shape of the connection head 302 allows for use of the same tracking assembly on both the left and the right knee because the tracking assembly may be attached in two different orientations.

The upper collar 306 may provide a stop surface that engages the attachment assembly. The body 308 is shown as having a generally cylindrical shape, but other shapes may be used. The body 308 extends to a proximal end 312. There the lower collar 310 is adjacent to the proximal end 312. The combination of the proximal end 312 and the lower collar 310 may connect to and engage the surgical robot to provide a secure connection. The lower collar 310 may include a fastener hole 314 into which a fastener may be inserted to secure the connection member 300 to the surgical robot. Other connection mechanisms may be used as well.

A surgical robot system was described above that may be used in knee surgery. In that case the knee tracking array assembly 202 attached to the surgical robot may use an arm to place the knee tracking array 210 in the field of view of the tracking system camera along with the tracking array on the surgical tool and on the patient anatomy. The surgical robot may be used for other surgeries, such as for example, shoulder surgery. In this case, the existing knee tracking array assembly 202 does not place the tracking array 210 in the field of view of the tracking system camera along with the tracking arrays on the surgical tool and the patient anatomy. As a result a different tracking array may be used for shoulder or other surgeries. In order to provide a sterile environment, the connection member 300 is draped and then the tracking array may be attached to the connection member 300 over the drape.

FIGS. 4A-D illustrate top perspective, bottom perspective, top, and bottom views, respectively, of a first embodiment of a tracking array that may be used in shoulder or other robotic surgeries. The tracking array 400 includes a body 402 and array 414. The array 414 is generally triangular shaped extending from the body 402. The array 414 includes two tracking elements 412. A third tracking element 412 is found on the body 402. These tracking elements 412 function as previously described along with a tracking system to determine the precise location and orientation of the tracking array 400.

The body 402 is shown as substantially circular with the array 414 extending therefrom. The body 402 may take other shapes as well. The body 402 may include an attachment opening 406 that engages the connection member 300 extending from the surgical robot. Body extensions 410 that are members that extend from the underside of the body 402 help to form the attachment opening 406. Locking handles 404 extend from to top side and the bottom side of the tracking array 400. The locking handles 404 form a locking mechanism configured to engage the connection member 300 to securely fasten the tracking array 400 to the connection member 300. The locking handles 404 also help to define the attachment opening 406. The locking handles 404 have a distal end with a locking edge 416. The locking edge 416 engages the connection head 302 of the connection member 300 to form a secure connection between the tracking array 400 and the connection member 300. The locking handles 404 may slope towards one another as the distal end of the locking handles 404. The locking handles 404 are rotatably connected to the body 402. This connection may be implemented by a hinge or a flexible material connection to the body 402. The distal ends of the locking handles 404 may be biased towards one another. This may be facilitated by a biasing member such as a spring (not shown) or may be caused by the flexible material. This bias causes the locking handles 404 to grip the connection member 300 to form the secure connection. In order to release the tracking array 400 from the connection member 300, a user may squeeze the locking handles 404 together to release the connection member 300. Other locking mechanisms may be used as well to secure the tracking array 400 to the connection member 300.

The attachment opening 406 has a shape that is complementary to the shape of the connection member so as to properly orient the tracking array 400 and to ensure a secure connection. For example, the body extensions 410 may engage the flat surfaces 304 on the connection head 302. Further, the locking edge 416 may engage the engagement surfaces 316 on the connection member 300.

The body 402 may also include windows 408. Windows 408 allow a user to verify that the tracking array 400 has completely and securely engaged the connection member 300 because the user can see that the connection head 302 appears in the windows 408.

Figure 5A:
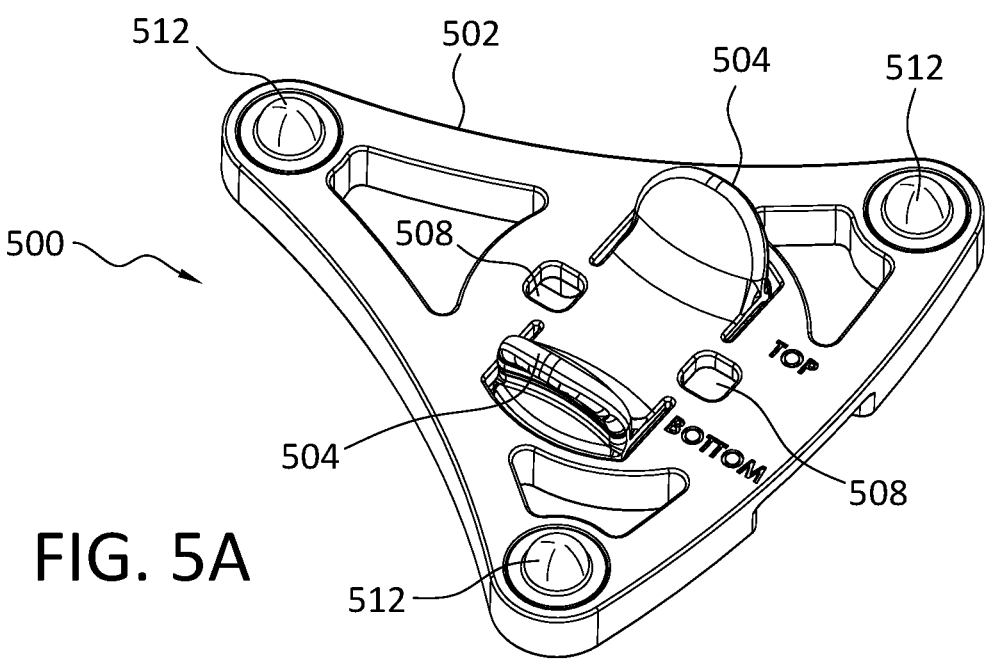
FIGS. 5A-D illustrate top perspective, bottom perspective, top, and bottom views, respectively, of a second embodiment of a tracking array that may be used in shoulder or other robotic surgeries.
Figure 5B:
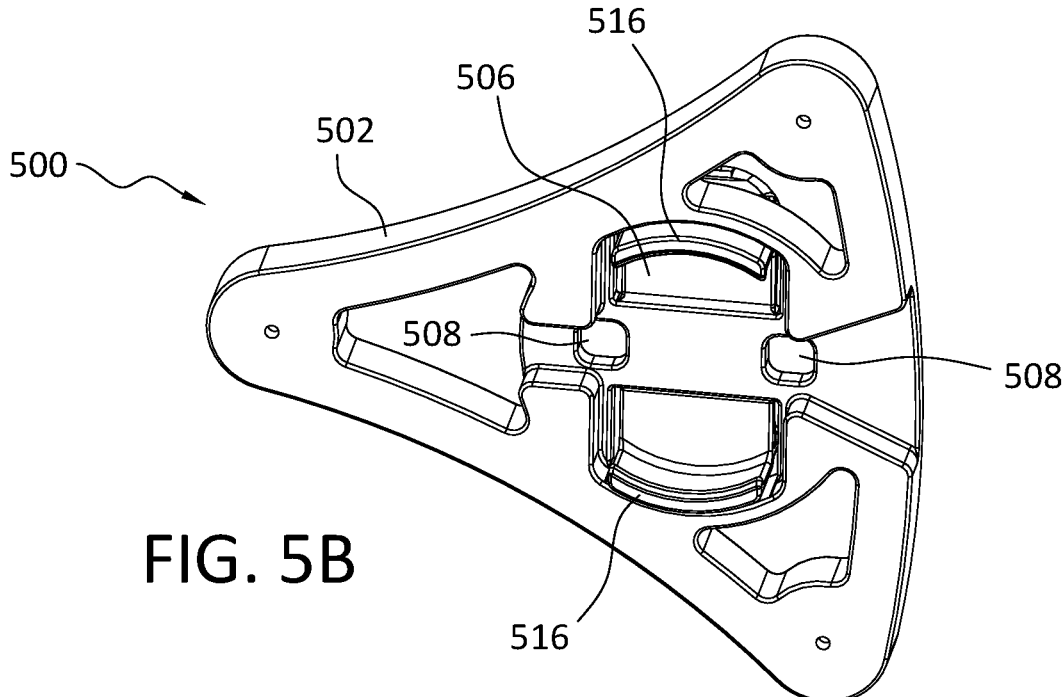
Figure 5C:
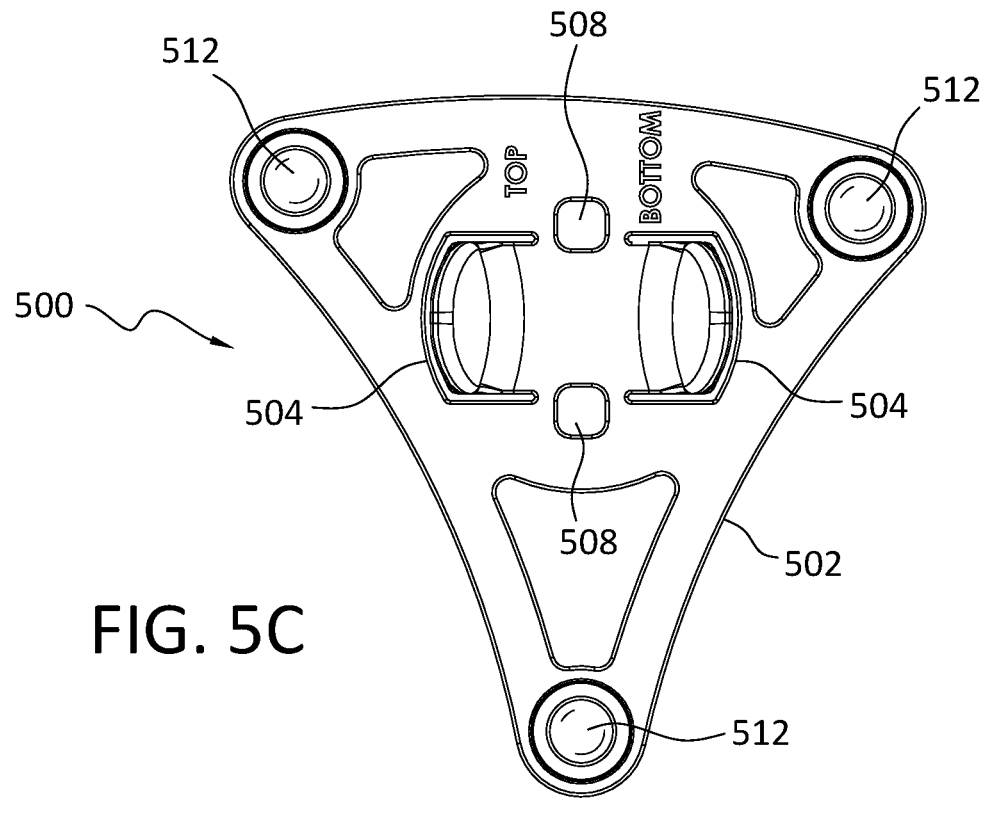
Figure 5D:
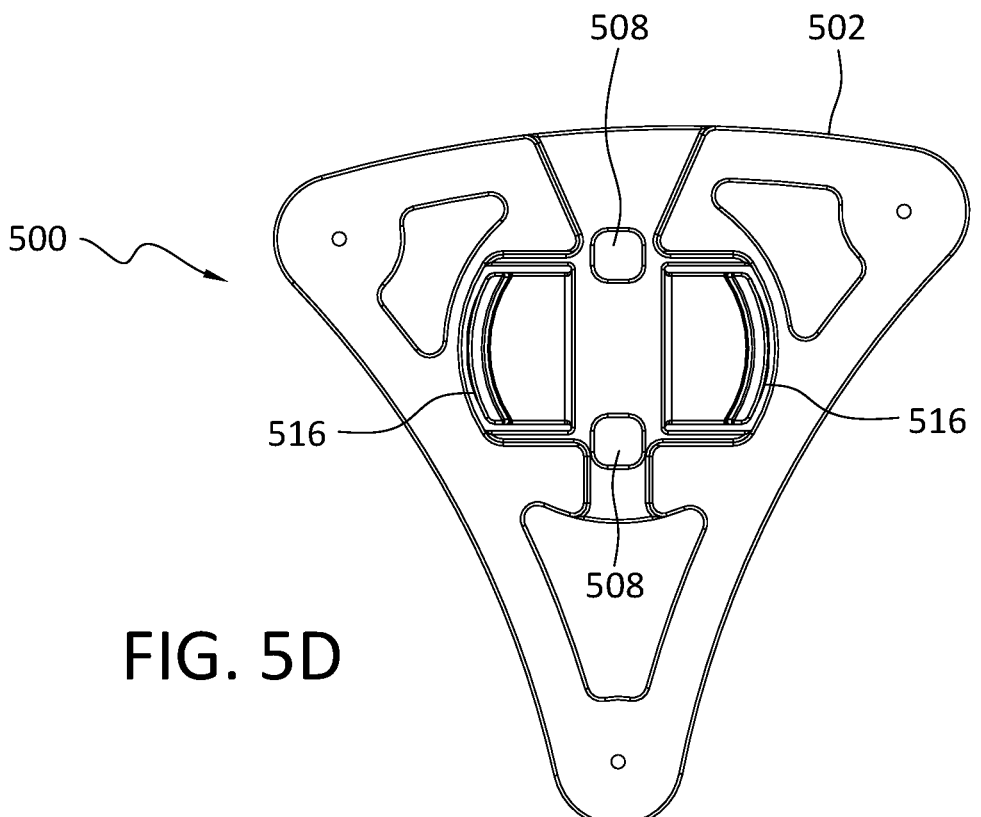

FIGS. 5A-D illustrate top perspective, bottom perspective, top, and bottom views, respectively, of a second embodiment of a tracking array that may be used in shoulder or other robotic surgeries. The tracking array 500 includes a body 502. The body 502 is generally triangular shaped as illustrated in FIG. 5A. The body 502 may take other shapes as well. The body 502 includes three tracking elements 512. These tracking elements 512 function as previously described along with a tracking system to determine the precise location and orientation of the tracking array 400. The three tracking elements 512 are illustrated as being near the corners of the triangular body in FIG. 5A. The three tracking elements 512 may be in other location on the body as well.

The body 502 may include an attachment opening 506 that engages the connection member 300 extending from the surgical robot. The attachment opening 506 may lie within a triangle formed by the three tracking elements 512. Alternatively, attachment opening 506 may be substantially centered on the body 502 or among the three tracking elements 512. Substantially centered may mean that the center is within 5% to 15% of a radius from the center of the body 502 or from the center of the three tracking elements 512 to one of the three tracking elements 512. Locking handles 504 extend from to top side and the bottom side of the tracking array 500. The locking handles 504 form a locking mechanism configured to engage the connection member 300 to securely fasten the tracking array 500 to the connection member 300. The locking handles 504 also help to define the attachment opening 506. The locking handles 504 have a distal end with a locking edge 516. The locking edge 516 engages the connection head 302 of the connection member 300 to form a secure connection between the tracking array 500 and the connection member 300. The locking handles 504 may slope towards one another as the distal end of the locking handles 504. The locking handles 504 are rotatably connected to the body 502. This connection may be implemented by a hinge or a flexible material connection to the body 502. The distal ends of the locking handles 504 may be biased towards one another. This may be facilitated by a biasing member such as a spring (not shown) or may be caused by the flexible material. This bias causes the locking handles 504 to grip the connection member 300 to form the secure connection. In order to release the tracking array 500 from the connection member 300, a user may squeeze the locking handles 504 together to release the connection member 300. Other locking mechanisms may be used as well to secure the tracking array 500 to the connection member 300.

The attachment opening 506 has a shape that is complementary to the shape of the connection member so as to properly orient the tracking array 500 and to ensure a secure connection. The locking edge 516 may engage the engagement surfaces 316 on the connection member 300. As described above, the shape of the connection head 302 allows for use of the same tracking assembly on both the left and the right knee because the tracking assembly may be attached in two different orientations.

The body 502 may also include windows 508. Windows 508 allow a user to verify that the tracking array 500 has completely and securely engaged the connection member 300 because the user can see that the connection head 302 appears in the windows 508.

Figures 6A, 6B:
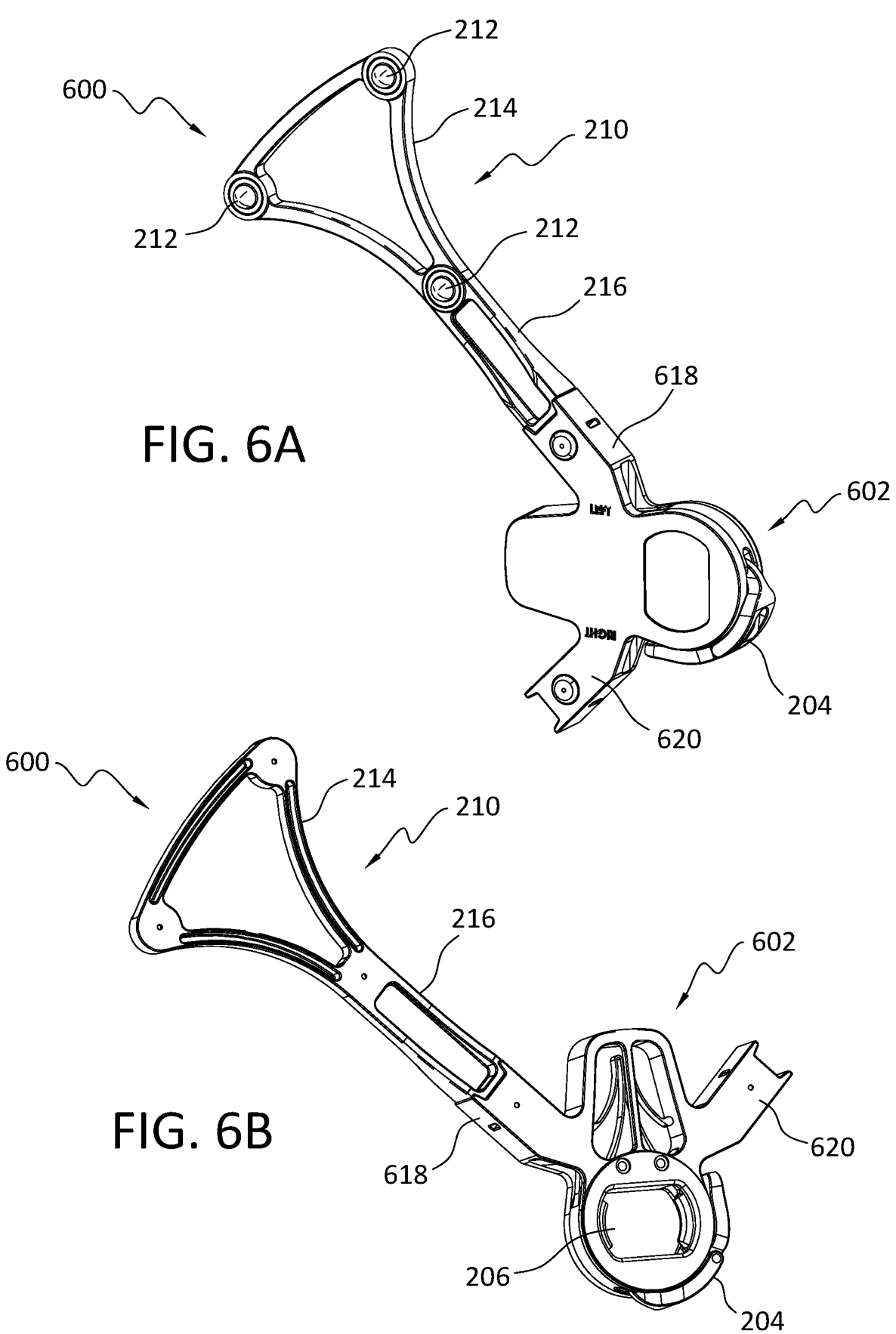
FIGS. 6A-B illustrate top perspective and bottom perspective views, respectively, of a third embodiment of a tracking array that may be used in shoulder or other robotic surgeries.

FIGS. 6A-B illustrate top perspective and bottom perspective views, respectively, of a third embodiment of a tracking array that may be used in shoulder or other robotic surgeries. The tracking array assembly 600 uses tracking array 210 from FIGS. 2A-C attached to a body 602. The tracking array 210 is described above with respect to FIGS. 2A-C. The body 602 may include attachment opening 206 along with locking lever 204 as found in tracking arm 200 and as described above. The body 602 may include first extension arm 618 and second extension arm 620. The first extension arm 618 and second extension arm 620 may connect to array frame 214 to form the tracking array assembly 600. The use of first extension arm 618 and second extension arm 620 allow for the array frame 214 to take on two different orientations relative to body 602. This embodiment allows for the reuse of array frame 214 in other types of surgeries with different fields of view. It also provides the option for two different orientations.

The tracking array embodiments described above allow for a surgical robot that may be used for various types of surgery requiring different fields of view. The system may include the surgical robot with a connection member 300 attached to it. Then a drape may be placed over the surgical robot including the connection member 300. A knee tracking array assembly 202 may be attached to the connection member 300 of the surgical robot over the drape. The surgical system may be registered and calibrated using the tracking system and known methods. Then a knee surgery may be carried out. When the surgical robot is used for a next surgery, it is determined that a different type of surgery is being performed that requires the use of a different tracking assembly because the field of view for the surgery is different. Next, the knee tracking array assembly 202 may be removed from the surgical robot. Then a new drape is placed over the connection member 300. Next, a tracking array 400, 500 or tracking array assembly 600 may be attached to the connection member 300. The surgical system is then calibrated using the tracking array 400, 500 or tracking array assembly 600. Then another type of surgery with a different field of view may be carried out using the surgical robot. This system allows for a single surgical robot to be used for different types of surgeries that have different fields of view. It means that the single surgical robot may have greater versatility and higher utilization as it may be used for various types of surgery.

The computer assisted surgical system may include a computer or processor system that controls the computer assisted surgical system. This computer system may include software for carrying the various functions of the computer assisted surgical system. For example, the computer system may run software that may detect the type of tracking array that has been attached to the surgical robot. Each of the different types of tracking arrays may have unique geometries that the computer system can identify. Each of the different tracking arrays may be associated with different surgical procedure (e.g., shoulder, knee, etc.). The computer system may then automatically run a specific functionality associated with the surgical procedure. Alternatively, if the user has selected a specific surgical procedure to carry out using the computer assisted surgical system, the computer system can determine if the array attached to the robot arm is the proper tracking array for the selected procedure.

While each of the embodiments are described above in terms of their structural arrangements, it should be appreciated that the invention also covers the associated methods of using the embodiments described above.

Although the various exemplary embodiments have been described in detail with particular reference to certain exemplary aspects thereof, it should be understood that the invention is capable of other embodiments and its details are capable of modifications in various obvious respects. As is readily apparent to those skilled in the art, variations and modifications and combinations of the various embodiments can be affected while remaining within the spirit and scope of the invention. Accordingly, the foregoing disclosure, description, and figures are for illustrative purposes only and do not in any way limit the invention, which is defined only by the claims.

What is claimed is:

1. A surgical system, comprising:
a surgical robot;
a connector coupled to the surgical robot, the connector configured and adapted to mate with tracking array assemblies;
a line-of-sight spatial camera;
a first tracking array assembly having a plurality of first trackers, the first tracking array assembly configured to mate with the connector wherein when the first tracking array assembly is mated to the connector the plurality of first trackers are located in first spatial positions relative to the surgical robot, the plurality of first trackers configured to be visible to the line-of-sight spatial camera; and
a second tracking array assembly having a plurality of second trackers, the second tracking array assembly configured to mate with the connector wherein when the second tracking array assembly is mated to the connector the plurality of second trackers are located in second spatial positions relative to the surgical robot, the plurality of second trackers configured to be visible to the line-of-sight spatial camera,
wherein the first spatial positions relative to the surgical robot are different from the second spatial positions relative to the surgical robot,
wherein the first tracking array assembly is configured and adapted for use in a first clinical application and the second tracking array assembly is configured and adapted for use in a second clinical application, wherein the first clinical application is different than the second clinical application, and wherein the first tracking array assembly comprises:
a body with a window configured to view the connector when the first tracking array assembly is connected to the connector.

2. The surgical system of claim 1, wherein a first tracking array assembly of the plurality of tracking array assemblies is configured to be used for a knee surgery.

3. The surgical system of claim 2, wherein a second tracking array assembly of the plurality of tracking array assemblies is configured to be used for a shoulder surgery.

4. The surgical system of claim 1, further comprising a drape between the connector and one of the first tracking array assembly and the second tracking array assembly.

5. A tracking array assembly for use with a surgical system, comprising:
a body with a window configured to view a connection member when the tracking array assembly is connected to the connection member;
a locking mechanism on the body including locking handles configured to engage the connection member and to securely fasten the tracking array assembly to the connection member;
a first tracking element on the body;
a frame extending from the body; and
a second tracking element and a third tracking element on the frame.

6. The tracking array assembly of claim 5, wherein the body includes an attachment opening formed by the locking handles and body extensions.

7. The tracking array assembly of claim 5, wherein locking handles include a locking edge configured to grip an engagement surface of the connection member.

8. The tracking array assembly of claim 5, wherein locking handles are rotatably connected to the body and configured to actuated to disconnect the tracking array assembly from the connection member.

9. A tracking array assembly for use with a surgical system, comprising:
a body with a window configured to view a connection member when the tracking array assembly is connected to the connection member;
a locking mechanism on the body including locking handles configured to engage the connection member and to securely fasten the tracking array assembly to the connection member;
three tracking elements on the body; and
an attachment opening on the body.

10. The tracking array assembly of claim 9, wherein locking handles include a locking edge configured to grip an engagement surface of the connection member.

11. The tracking array assembly of claim 9, wherein locking handles are rotatably connected to the body and configured to actuated to disconnect the tracking array assembly from the connection member.

12. The tracking array assembly of claim 9, wherein ends of the locking handles that engage the connection member are rotatably connected to the body and configured to actuated to disconnect the tracking array assembly from the connection member.

13. The tracking array assembly of claim 9, wherein the attachment opening lies within a triangle formed by the three tracking elements.

14. The tracking array assembly of claim 9, wherein the attachment opening is substantially centered on the body.

15. The tracking array assembly of claim 9, wherein the attachment opening is substantially centered among the three tracking elements.

16. A method of using a surgical system including a surgical robot; a connection member connected to the surgical robot; a first and second tracking array assemblies configured to engage the connection member wherein the first and second tracking array assemblies provide different fields of view for a tracking system, comprising:

determining that a surgery to be performed by the surgical system requires the use of the second tracking array assembly;

removing the first tracking array assembly from the surgical robot;

attaching the second tracking array assembly to the surgical robot; and calibrating the surgical system using the second tracking array assembly, wherein the first tracking array assembly comprises:

a body with a window configured to view a connection member when the first tracking array assembly is connected to the connection member.

17. The method of claim 16, comprising performing the surgery using the second tracking array assembly.

18. The method of claim 16, wherein the first tracking array assembly is used for knee surgery and the second tracking array assembly is used for a different surgery.

19. The method of claim 18, wherein the different surgery is shoulder surgery.

20. The method of claim 18, wherein the different surgery is knee surgery.

21. The method of claim 16, wherein the first tracking array assembly is used for shoulder surgery and the second tracking array assembly is used for a different surgery.

*     *     *     *     *